United States Patent
Wong

(10) Patent No.: US 11,696,693 B2
(45) Date of Patent: Jul. 11, 2023

(54) APPARATUS FOR MONITORING THE PULSE OF A PERSON AND A METHOD THEREOF

(71) Applicant: Well Being Digital Limited, Shatin (HK)

(72) Inventor: Ming Yip Wallace Wong, Shatin (HK)

(73) Assignee: WELL BEING DIGITAL LIMITED, Sha Tin (HK)

( * ) Notice: Subject to any disclaimer, the term of this patent is extended or adjusted under 35 U.S.C. 154(b) by 1186 days.

(21) Appl. No.: 16/309,106

(22) PCT Filed: Jun. 20, 2018

(86) PCT No.: PCT/CN2018/091981
§ 371 (c)(1),
(2) Date: Dec. 11, 2018

(87) PCT Pub. No.: WO2018/233625
PCT Pub. Date: Dec. 27, 2018

(65) Prior Publication Data
US 2020/0281484 A1    Sep. 10, 2020

(30) Foreign Application Priority Data

Jun. 21, 2017  (HK) ................................. 17106213.9
Aug. 2, 2017   (HK) ................................. 17107689.2

(51) Int. Cl.
*A61B 5/00* (2006.01)
*A61B 5/02* (2006.01)
(Continued)

(52) U.S. Cl.
CPC .............. *A61B 5/0245* (2013.01); *A41B 1/08* (2013.01); *A41D 1/002* (2013.01);
(Continued)

(58) Field of Classification Search
CPC ....... A61B 5/0059; A61B 5/25; A61B 5/6804; A61B 5/6805; A61B 5/6802; A61B 5/6801; A61B 5/68
See application file for complete search history.

(56) References Cited

U.S. PATENT DOCUMENTS 6,047,203 A    4/2000  Sackner et al.
8,560,044 B2   10/2013 Kurzweil et al.
(Continued)

FOREIGN PATENT DOCUMENTS

CN    86201904 U    10/1987
CN    1933777 A     3/2007
(Continued)

OTHER PUBLICATIONS

Foreign Communication from a Related Counterpart Application, International Search Report and Written Opinion dated Sep. 13, 2018, International Application No. PCT/CN2018/091981 filed on Jun. 20, 2018.
(Continued)

*Primary Examiner* — Jon Eric C Morales

(57) ABSTRACT

A wearable device in the form of a tee-shirt is described. The sleeves of the tee-shirt having an electrocardiogram (ECG) sensor, a photoplethysmogram (PPG) sensor or a ballistocardiogram (BCG) sensor for monitoring the pulse of a person wearing the tee-shirt. The tee-shirt makes possible the comparison of the pulses down the two arms. The pulse-transit-time, pulse amplitude, pulse spread and pulse shape may be compared to observe any difference between the left and right sides of the person.

6 Claims, 12 Drawing Sheets

(51) Int. Cl.

| | | |
|---|---|---|
| *A61B 5/021* | (2006.01) | |
| *A61B 5/022* | (2006.01) | |
| *A61B 5/0245* | (2006.01) | |
| *A61B 5/024* | (2006.01) | |
| *A61B 5/11* | (2006.01) | |
| *A41D 1/00* | (2018.01) | |
| *A41B 1/08* | (2006.01) | |

(52) U.S. Cl.
CPC ...... *A61B 5/02427* (2013.01); *A61B 5/02438* (2013.01); *A61B 5/1102* (2013.01); *A61B 5/6804* (2013.01)

(56) References Cited

U.S. PATENT DOCUMENTS

| | | |
|---|---|---|
| 2002/0026120 A1 | 2/2002 | Ogura et al. |
| 2016/0095527 A1* | 4/2016 | Thng .................. A61B 5/339 600/382 |
| 2016/0220122 A1 | 8/2016 | Luna et al. |

FOREIGN PATENT DOCUMENTS

| | | |
|---|---|---|
| CN | 201591554 U | 9/2010 |
| CN | 101919692 A | 12/2010 |
| CN | 102743160 A | 10/2012 |
| CN | 205794911 U | 12/2016 |
| CN | 206080496 A | 4/2017 |
| CN | 206080496 U | 4/2017 |
| CN | 106691414 A | 5/2017 |
| CN | 106999083 A | 8/2017 |
| CN | 110868922 A | 3/2020 |
| JP | 2014012839 A | 1/2014 |
| WO | 2011045806 A1 | 4/2011 |
| WO | 2012103296 A2 | 8/2012 |
| WO | 2014012839 A1 | 1/2014 |
| WO | 2017081353 A1 | 5/2017 |

OTHER PUBLICATIONS

Foreign Communication From a Related Counterpart Application, Chinese Office Action dated Dec. 16, 2021, Chinese Application No. 201880041751.4 filed on Jun. 20, 2018.

* cited by examiner

APPARATUS FOR MONITORING THE PULSE OF A PERSON AND A METHOD THEREOF

CROSS-REFERENCE TO RELATED APPLICATIONS

The present application is a filing under 35 U.S.C. 371 as the National Stage of International Application No. PCT/CN2018/091981, filed Jun. 20, 2018, entitled "AN APPARATUS FOR MONITORING THE PULSE OF A PERSON A METHOD THEREOF," which claims priority to Hong Kong Application No. HK 17106213.9 filed with the Intellectual Property Office of Hong Kong on Jun. 21, 2017 and entitled "AN APPARATUS FOR MONITORING THE PULSE OF A PERSON A METHOD THEREOF," and Hong Kong Application No. HK 17107689.2 filed with the Intellectual Property Office of Hong Kong on Aug. 2, 2017 and entitled "AN APPARATUS FOR MONITORING THE PULSE OF A PERSON A METHOD THEREOF," each of which are incorporated herein by reference in their entirety for all purposes.

FIELD OF THE INVENTION

The current invention relates to devices and methods for measuring heart rate, and particularly devices providing electrocardiogram (ECG), ballistocardiogram (BCG) and photoplethysmogram (PPG) measurements.

BACKGROUND

Heart rate measurement is done typically using electrocardiogram (ECG) by placing electrodes on the body, about and around the heart. The electrodes monitor electrical signals which are then used to chart a signal, which shows the stages of a heartbeat, typically the contraction and relaxation of the different heart chambers.

However, applying electrodes to a person to obtain an ECG is not practical for long term, round-the-clock monitoring, as the person has to remain by the ECG machine to which the electrodes are attached. Furthermore, the application of electrodes onto the body is done using adhesive tape which irritates the skin. The tape tend to fall off after a while, which can disrupt the ECG reading.

Yet, it would be useful to monitor some people with high risk of cardiac arrest for long, extended periods of time, either for preventative care or for academic research.

Therefore, it is desirable to provide an apparatus and accompanying methods by which a person may be monitored for his ECG over a relatively long period of time.

Furthermore, in using ECG or PPG to monitor the pulse of a person, there is an underlying assumption that blood flow or cardiac performance observed from one part of the body is representative of the whole body. However, this is not quite the case in reality. For example, blood clot problems such as thrombosis are localised problems, but these locations are not discoverable by typical application of ECG or PPG.

Hence, it is also desirable to improve the applications of ECG and PPG technologies, in novel and inventive applications to bring about better health monitoring.

STATEMENTS OF INVENTION

In a first aspect, the invention proposes an apparatus for measuring the heart rate of a person, comprising a piece of vestment suitable for being worn on the body of the person; the vestment has two sleeves, each suitable for the person's respective arms to be inserted through; each of the sleeves having a tightened band for hugging the bicep of the respective arm, the tightening provided by a resilient material; one or more electrode for contacting the skin of the respective bicep in the band of each of the sleeves; an electrical conductor extending across the vestment connecting the electrodes of the band of each of the sleeves.

In a second aspect, the invention proposes an apparatus for measuring the heart rate of a person, comprising a piece of vestment suitable for being worn on the body of the person; the vestment has at least one sleeve suitable for one of the person's two arms to be inserted through; the sleeves having a tightened band for hugging the bicep of the arm, the tightening provided by a resilient material; an photoplethysmogram (PPG) sensor in the band; such that the resilient material urges the photoplethysmogram (PPG) into contact with the skin of the bicep.

In a third aspect, the invention proposes an apparatus for measuring the heart rate of a person, comprising a piece of vestment suitable for being worn on the body of the person; the vestment has two sleeves, each suitable for the person's respective arms to be inserted through; each of the sleeves having a tightened band for hugging the bicep of the respective arm, the tightening provided by a resilient material; one or more electrode for contacting the skin of the respective bicep in the band of each of the sleeves; an electrical conductor extending across the vestment connecting the electrodes of the band of each of the sleeves.

In a fourth aspect, the invention proposes an apparatus for measuring the heart rate of a person, comprising a piece of vestment suitable for being worn on the body of the person; the vestment has at least one sleeve suitable for one of the person's two arms to be inserted through; the sleeves having a tightened band for hugging the bicep of the arm, the tightening provided by a resilient material; an photoplethysmogram (PPG) sensor in the band; such that the resilient material urges the photoplethysmogram (PPG) into contact with the skin of the bicep.

The movements of the user do not dislocate the electrocardiogram (ECG) or the photoplethysmogram (PPG) from contacting his skin. As tee-shirts are not easily seen, especially if worn as an undergarment, and is less prone to collecting sweat as in the leather band of a watch, the embodiments allow twenty-four hour wearing and monitoring of the heartbeat of the wearer. Advantageously, subtle information such as heart rate variations (HRV) can be monitored for a person round the clock. Even if there were data obtained by embodiments during moments which could render the data inaccurate, such as when the person wearing the tee-shirt adjusts the sleeves, the round-the-clock data means the person is better off over-sampled than not. The person making deductions or analysis based on the data can reject any clearly inaccurate data and would still have data made over disconnected but continual, lengthy periods of observations. Such continuous monitoring is crucial for monitoring people with high risk of sudden cardiac arrests, or for research purposes.

An apparatus for monitoring the pulse of a person, comprising a piece of clothing suitable for being worn on the body of the person; the clothing having two sleeves, each suitable for the person's respective limbs to be inserted through; along each of the sleeves is a stretchable neck for hugging the respective limb; one or more electrodes in each neck; an electrical conductor connecting the electrodes of each neck; wherein the neck urges the electrodes of each of the sleeve into contact with the skin of the respective limb.

An electrocardiogram (ECG) monitor in the form of a wearable clothing or vestment allows a person to wear it over a long period of time to have his pulse monitored, even for a couple of days. The stretchable neck provides a sort of band around the arm which presses the electrodes against the skin, maintaining consistent and reliable contact in spite of any movements of the person or any flexing of the arm.

An apparatus for monitoring the pulse of a person, comprising a piece of clothing suitable for being worn on the body of the person; the clothing having least one sleeve suitable for at least one of the person's limbs to be inserted through; the at least one sleeve having a resilient neck for hugging the limb; one or more photoplethysmogram (PPG) sensors in the neck; such that the neck urges the one or more photoplethysmogram (PPG) sensors into contact with the skin of the limb.

In this aspect, the stretchable neck provides a sort of band around the arm which presses the photoplethysmogram (PPG) sensors against the skin, maintaining consistent and reliable contact in spite of any movements of the person or any flexing of the arm. This permits round the clock use of photoplethysmogram (PPG) sensors to monitor the pulse of the person.

Preferably, the clothing comprises at least two sleeves, each sleeve for the respective opposite limbs of the person to be inserted through.

This provides the possibility of having a photoplethysmogram (PPG) device on each opposite limb. This provides that information on the pulse transit time in each limb to be monitored. Pulse transit time is the time taken for the surge of blood caused by a heartbeat to reach a limb. Additionally, this allows the shape, the spread and the amplitude of the pulses can be compared.

Typically, the limbs are the arms of the person. Alternatively, the limbs are legs of the person. Therefore, 'sleeves' in this description is not limited to sleeves of clothing of the upper body, but 'sleeves' also include the legs of clothing intended to be worn on the lower body.

Preferably, the neck of each sleeve further comprises an electrocardiogram (ECG) electrode; an electrical conductor connecting the electrodes of each neck to form a closed circuit across the person's body; and the neck of each sleeve urging the electrocardiogram (ECG) electrode into contact with the skin of the limb.

Furthermore, it is also preferable, that the apparatus comprises a ballistocardiogram (BCG) sensor.

Furthermore, it is also preferable, that the apparatus comprises a microcontroller configured to identify the electrocardiogram (ECG) pulse and photoplethysmogram (PPG) pulses as being from the same heartbeat.

Typically, the device comprises a microcontroller configured to identify the ballistocardiogram (BCG) pulse and photoplethysmogram (PPG) pulses as being from the same heartbeat.

The limbs are typically the arms of the person. Alternatively, the limbs are the legs of the person.

In yet another aspect, the invention proposes a method of monitoring heart pulses of a person, comprising the steps of: obtaining the left pulse of a heartbeat in the left limb; obtaining the right pulse of the same heartbeat in the right limb; observing a difference between the pulses in one or more of the following pulse characteristic: i) the pulse-transit-time of the pulse; ii) the spread of the pulse; iii) the trough to peak amplitude of the pulse; iv) the shape of the pulse.

Preferably, the left pulse of a heartbeat in the left limb is obtained by photoplethysmogram (PPG), and the right pulse of the same heartbeat in the right limb is obtained by photoplethysmogram (PPG).

This method is not limited to any specific apparatus which has to be worn as a piece of clothing. Two wrist-worn photoplethysmogram (PPG) sensors may be used instead, as long as pulses can be identified as being of the same heartbeat. This is possible because heartbeat propagation into the limbs is never so slow that the pulse of one heartbeat is still reaching the extremity of a limb when a subsequent heartbeat commences. The photoplethysmogram (PPG) sensors can have wireless transceiver to send data to a common processing apparatus such as smartphone to compare the pulses.

Preferably, the method further comprises the step of: obtaining an electrocardiogram (ECG) pulse of the same heartbeat by electrocardiogram (ECG); wherein the pulse-transit-time of the left pulse is referenced from the electrocardiogram (ECG) pulse; the pulse-transit-time of the right pulse is referenced from the electrocardiogram (ECG) pulse.

If both sides of the body have similar constrictions, artery clogging and so on, there may be no difference in the pulses on the two limbs. In this case, the absolute pulse-transit-time may shed light on potential problem in the body as a whole.

Preferably, the method further comprises the steps of: obtaining a ballistocardiogram (BCG) pulse of the same heartbeat by ballistocardiogram (BCG); wherein the pulse-transit-time of the left pulse is referenced from the ballistocardiogram (BCG) pulse; the pulse-transit-time of the right pulse is referenced from the ballistocardiogram (BCG) pulse.

Typically, the limbs are the arms of the person. Alternatively, however, the left limb is the left leg of the person; and the right limb is the right leg of the person, in particular, the left pulse of a heartbeat in the left limb is obtained from the left calf; and the right pulse of the same heartbeat in the right limb is obtained from the left calf.

BRIEF DESCRIPTION OF DRAWINGS

It will be convenient to further describe the present invention with respect to the accompanying drawings that illustrate possible arrangements of the invention, in which like integers refer to like parts. Other embodiments of the invention are possible, and consequently the particularity of the accompanying drawings is not to be understood as superseding the generality of the preceding description of the invention.

DESCRIPTION OF PREFERRED EMBODIMENTS

Figure 1:
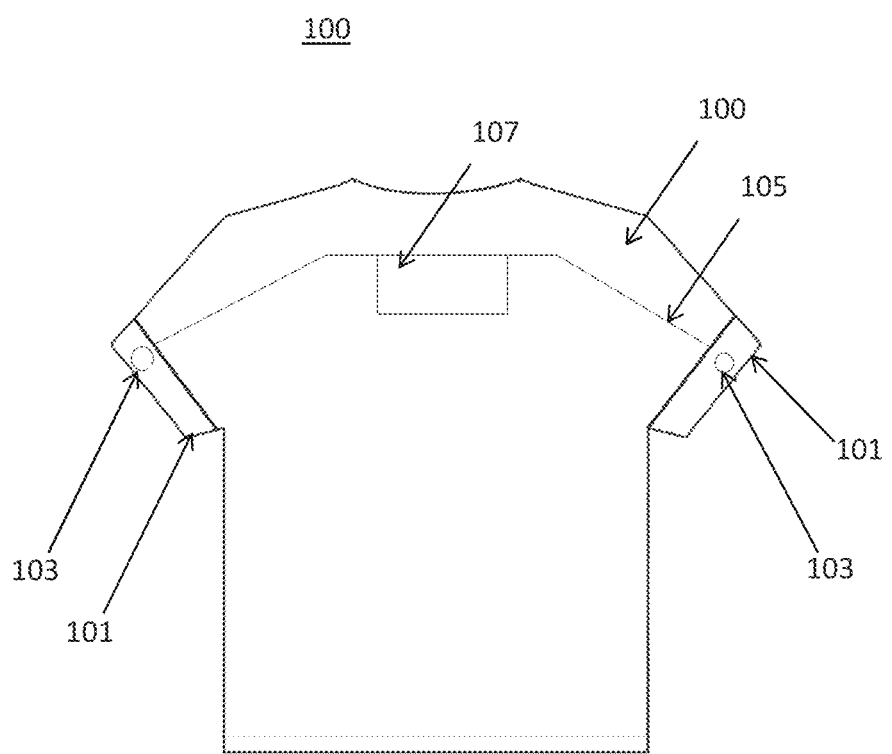
FIG. 1 shows an embodiment of the invention.

FIG. 1 shows an embodiment 100 of the invention, which is a tee-shirt, for obtaining the electrocardiogram (ECG) of the person wearing it. The tee-shirt 100 has two short sleeves 101. The edge of each of the sleeves 101 is lined with a resilient, stretchable material, such as an elastic band or Lycra (an elastic polyurethane fibre or fabric used especially for close-fitting sports clothing, also known as Spandex).

In the edge of each sleeve 101 is placed an ECG electrode 103. The electrode 103 is held in close contact with the skin of any one who is wearing the tee-shirt. This allows movement of the user's arm, including repositioning and flexing of the muscles, without causing the electrode 103 to become out of contact with the person's skin.

The view of FIG. 1 is the back of the tee-shirt 100 instead of the front, which is why only the back collar is seen. A conductive element, such as a wire 105, is shown connecting the electrodes 103 to a flexible printed circuit board 107. Hence, the printed circuit board 107 lays against the upper back of the person, where the printed circuit board 107 is the least likely to be in the way of most of the person's movements.

The printed circuit board 107 is preferably provided with a battery for operation of the electrodes 103 and any processor in the printed circuit board 107, as well as any wireless communication transceiver for communicating with a smart phone, computer or a remote server.

Having an electrode 103 on both biceps connected by the wire 105 creates a closed circuit through the electrodes 103 across the body and heart of the person wearing the tee-shirt. The closed circuit is then useable for monitoring heart related electric signals to obtain an ECG.

The wire connecting the electrode 103 to the flexible printed circuit board 107 is preferably of the type that is thin and thread like, such that it may be woven into the fabric of the tee-shirt to behave as an integral, flexible part of the tee-shirt.

Wires can be made as thin as required depending on the choice of metals or alloys in an actual product embodying the invention. Gold has the highest conductivity and can be spun into very thin wires, but gold is expensive. Copper is one of the best wire material because it is very ductile and conductive. Another choice is silver, which is also very ductile and conductive. Yet another alternative is aluminium. Aluminium is less conductive than copper, having only about 61% of the conductivity of copper, but makes up for this shortcoming by being relatively lighter in weight.

The form of the wire can a cable with a circular cross section, however, flat wire strips (not illustrated) can also be used if a certain amount of rigidity is preferred. Flat wire strips are only easily bent about the flat face of the wire but not about the edge. Hence, flat wires can be used to provide some structure to the tee-shirt and prevent the wire from running away from its installed position. For example, all around the edge of the sleeve 101 can be lined with a flat wire. This will prevent the sleeve 101 from turning up, and cutting off contact between the wire and the person's skin The fabric which the tee-shirt is made of is preferably woven or knitted fabric such as jersey, which allows the tee-shirt to be stretchable and body hugging. This allows the wires threaded into the tee-shirt to be held as closely to the body as possible, preventing dislocation of the wires, and also preventing any abrasion. Having said that, this preference is not a necessary one. The bulk of the tee-shirt does not have to be stretchable and body hugging, as long as the resilient material in the sleeves 101 consistently maintains electrode 103 contact with the skin of the person wearing the tee-shirt.

An advantage of using resilient and stretchable material to provide the bands lining the edge of the sleeves 101 is that the resilient material can accommodate flexing of muscles without letting the electrodes 103 lift away from the skin.

Figure 2:
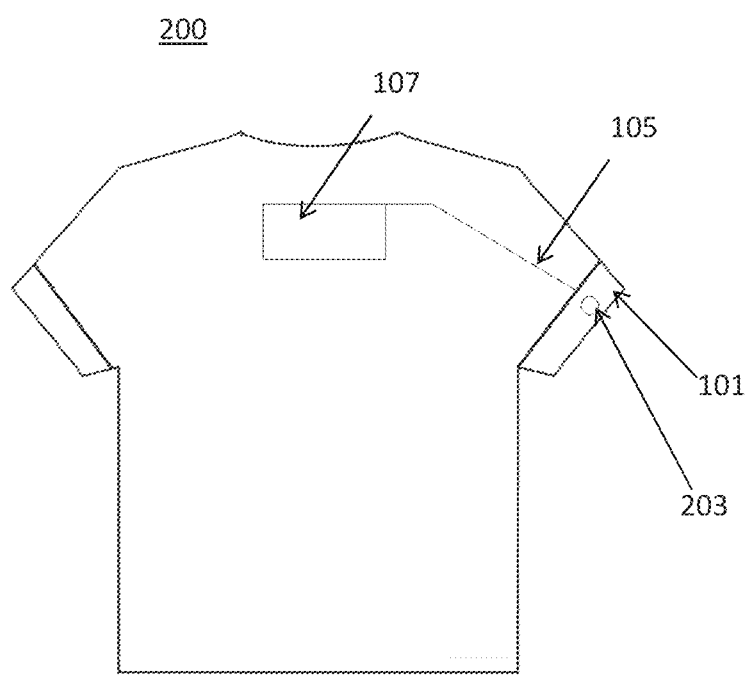
FIG. 2 shows a second embodiment of the invention.

FIG. 2 shows another embodiment 200 of the invention wherein, instead of the ECG, the device placed in the band in the sleeve 101 of the tee-shirt is a photoplethysmogram (PPG) sensor 203. As the skilled reader would know, a PPG sensor 203 monitors the pulsation of blood in the body by monitoring absorption and dispersion of light which has been sent into the skin and tissue of the body. As the content of blood in skin and tissue surges along with the pumping of the heart, the absorption of light varies in accordance to the fullness or depletion of blood in skin and tissue. Typically, any wavelength of light maybe used, from infra-red to visible light. However, it appears that green light and infrared light is the best choices for the purpose of reading blood volume surges. One advantage of using PPG is that unlike ECG there is no need to form a closed circuit across the heart of the person. Hence, in the simplest embodiments, only one sleeve 101 may be provided with an elastic band in which a PPG sensor 203 is embedded.

In FIG. 2, the tee-shirt has a wire extending from the printed circuit board 107 to the PPG, for controlling the PPG and collecting data from the PPG.

In both embodiments, the movements of the user do not dislocate the ECG or the PPG from contacting his skin. As tee-shirts are not easily seen if worn as an undergarment, the embodiments allow twenty four hours wearing and monitoring of the heartbeat of the person. This is particularly possible in a dry temperate or cold climate as the skin remains dry despite regular perspiration.

Figure 3:
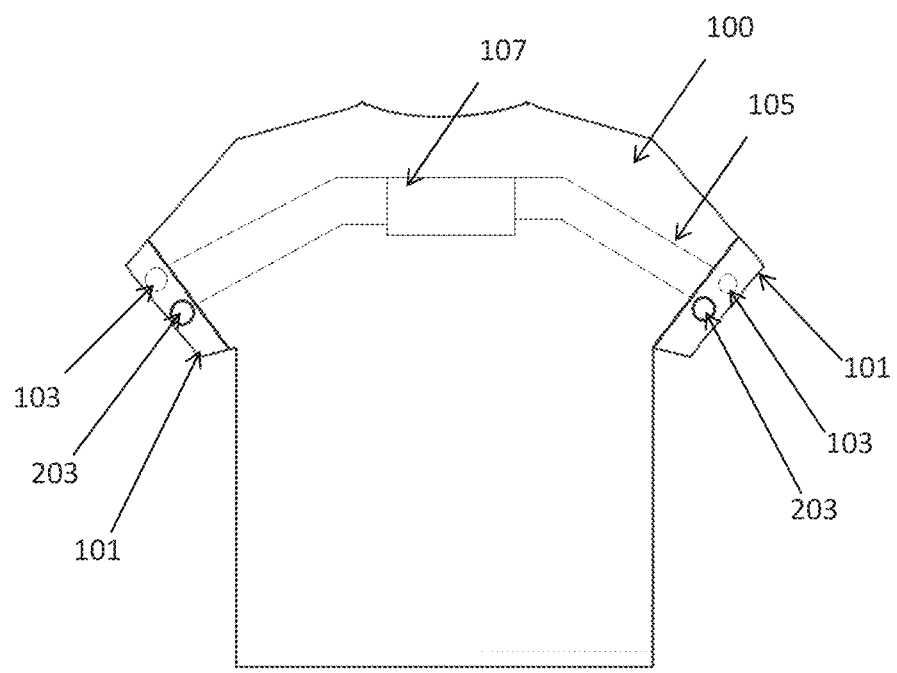
FIG. 3 shows a third embodiment of the invention.

In a further embodiment shown in FIG. 3, each sleeve 101 of the tee-shirt has a PPG sensor 203 as well as the electrodes 103 of for obtaining an ECG. Hence, for each bicep, an ECG can be obtained as well as a PPG. The ECG tells when a heartbeat takes place, while the PPG on each bicep shows how long does it take for the surge of blood to travel from the heart to the respective bicep, i.e. the pulse-transit-time to the bicep.

Anomalies in the left and right main arteries of the upper body may be monitored by observing the difference between the left and right pulse-transit-times.

Generally, the length of the blood vessels from the heart to the bicep may be assumed to be virtually the same for both biceps. Hence, left and right pulse-transit-times should be similar in a healthy individual. If the left and right pulse-transit-times are different by a significant amount, it may be indicative of blockage in some of the blood vessels, and it is suggesting an increased risk of heart disease and stroke. Alternatively, it could represent a tumour blocking blood flow. Furthermore, it could be indicative of uneven constriction between the left and right sides of the upper body. Yet further, it could mean the muscles on one side of the body have been overused or over-exercised. Such information is useful for doctors to zoom in on any left and right side imbalance, and also to physical trainers, chiropractors and osteopaths.

Figure 4:
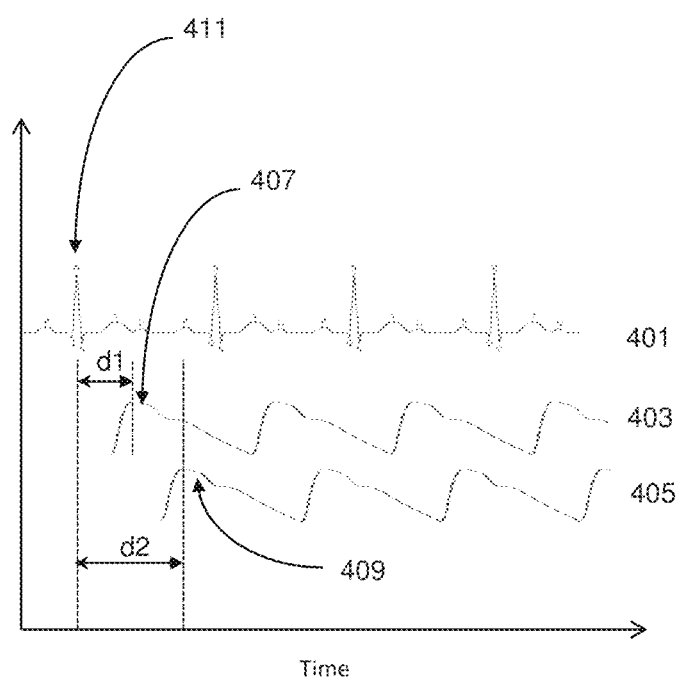
FIG. 4 shows readings which may be obtained by the embodiment of FIG. 3.

FIG. 4 illustrates how any anomaly between the left and right sides of a person may be observed using the embodiment.

FIG. 4 is a chart of the pulse of a person wearing the embodiment of FIG. 3. The top line 401 in the chart shows his ECG. The middle line 403 shows his PPG down the left bicep. The bottom line 405 shows his PPG down the right bicep. The ECG chart 401 is virtually instantaneous with his heartbeat. However, the PPG charts 403, 405 are time delayed because the surge of blood created by the heartbeat needs time to reach the biceps and extremities of the limbs, i.e. pulse-transit-time.

The pulse-transit-time between the PPG pulse down the left bicep 403 and the ECG 401 is shown as d1. The pulse-transit-time between the PPG pulse down the right bicep 405 and the ECG 401 is shown as d2. The peak 411 monitored by ECG and the peaks 407, 409 monitored by PPG all belong to the same heartbeat. If the person is healthy, d1 might equal d2.

It is possible to measure the time difference (i.e. d1–d2) between the PPG signals 403, 405 down both biceps directly, i.e. observe the peak 407 of the pulse on the right bicep and the peak 409 of the pulse on the left bicep and take their time difference to obtain d1–d2, without measuring their time difference with respect to the ECG peak 411. Nevertheless, it is preferable to monitor the pulses down each bicep 407, 409 with reference to the ECG peak 411 as time zero. This is because it is easier to identify an ECG peak in order to anticipate the corresponding PPG pulses 407, 409 down both biceps. Furthermore, if both sides of the body are just as blocked or constricted, there may not be any significant difference between d1 and d2, but the absolute pulse-transit-time between each PPG pulse 403, 405 and the ECG pulse 401 might show significant time lag, indicating a health warning.

Figure 5:
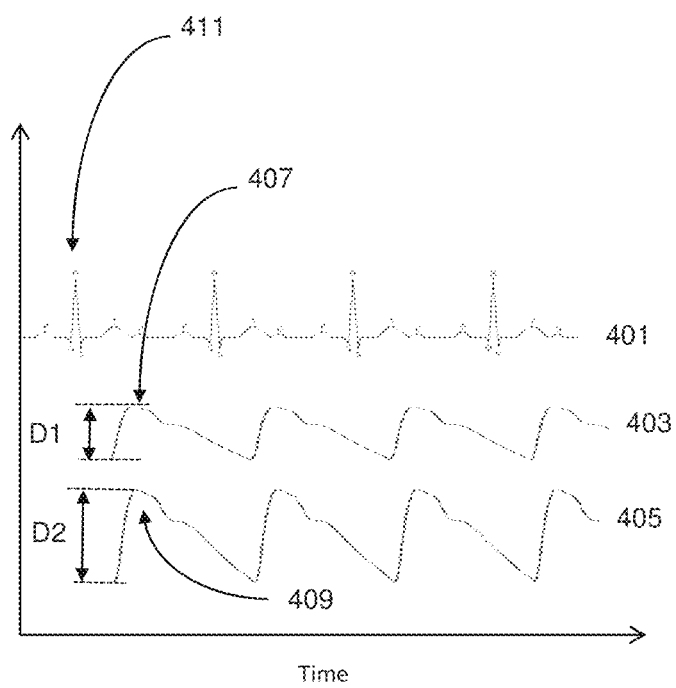
FIG. 5 shows further possible readings which may be obtained by the embodiment of FIG. 3.

FIG. 5 shows another way in which the PPG pulses 403, 405 between the two biceps may be compared. Whereas the chart in FIG. 4 shows how lag time between two PPG pulses 407, 409 may be used to observe differences between the left and right sides of the person's body, the chart in FIG. 5 shows how the intensity of the PPG pulses 403, 405 may be used. The example in FIG. 5 shows the trough-to-peak amplitude D1 of a pulse in the left bicep 403 being smaller than the trough-to-peak amplitude D2 of the pulse in the right bicep 405. In this example, no time lag is observed between the PPG peaks, 407, 409. This is possible in some cases because constriction in arteries may not necessarily translate into a slowing down of the pulse. A constriction may simply dampen the intensity of the pulse, leading to a weaker pulse signal. Physically, this means less blood content is pumped by each beat of the heart, hence the smaller amplitude. In FIG. 5, the pulse down the left bicep 403 is shown to have smaller trough-to-peak amplitude, whereas the pulse down the right bicep 405 has relatively greater trough-to-peak amplitude. The peak 411 of the ECG 401 is still useful as a trigger to anticipate the peaks 407, 409 of both PPG pulses 403, 405, ensuring that they are all of the same heartbeat.

Figure 5A:
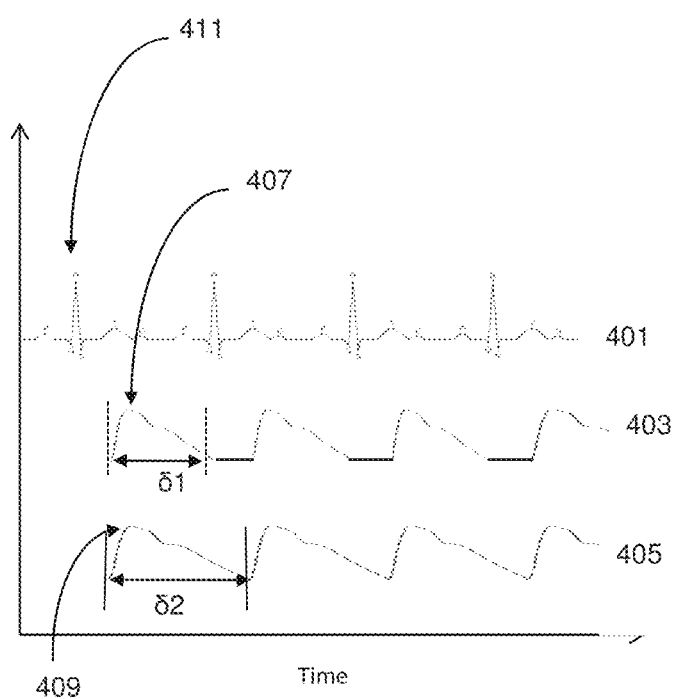
FIG. 5a shows further possible readings which may be obtained by the embodiment of FIG. 3.

FIG. 5a shows yet another way in which the PPG pulses 403, 405 between the two biceps may be compared. Whereas the chart in FIG. 4 shows how lag time between two PPG pulses 403, 405 may be used to observe difference between the left and right sides of the person's body, and whereas the chart in FIG. 5 shows how the intensity of the PPG pulses 403, 405 may be used, FIG. 5a shows how the difference in the spread of the pulses 403, 405 in the two biceps may be different and subject to comparison. FIG. 5a illustrates that the spread δ1 of the pulse 403 in the left bicep is less than the spread δ2 of the pulse 405 in the right bicep. This is possible because constriction in arteries may cause a pulse to be released into a bicep or limp in a drawn-out, spread pulse.

Besides comparing the time of the PPG pulses, or the spread of the pulses 403, 405, or the trough-to-peak amplitude of the pulses 403, 405, it is also possible to simply compare the shape of the pulses 403, 405. The peaks 407, 409 of the pulses can be easily classified into different categories of shape by using signal cross-correlation methods (not illustrated), wherein the template of a standard shape is applied to the pulses. If the shape of a pulse is a match to the template, a mathematical value of unity can be calculated. In this way, the shape of pulses down the left and right limb of the same heartbeat can be measured, characterised and compared. Cross-correlations methods are well-known signal processing techniques and do not require elaboration here.

Figure 6:
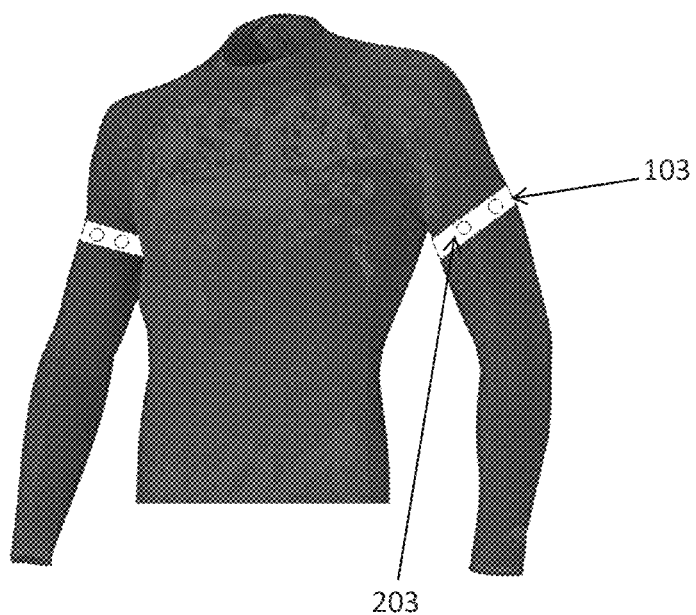
FIG. 6 shows a variation to the embodiment of FIG. 3.

FIG. 6 shows a variation of the embodiment of FIG. 3. Instead of a tee-shirt, the embodiment is now a diver's suit 601. FIG. 6 only shows the upper body part of the suit. As the diver's suit has long sleeves 101, mid-way along each sleeve 101 about the position of the bicep is a PPG sensor 203 as well as the electrodes 103 of for obtaining an ECG, in similar positions to the PPG sensors 203 and electrodes 103 in FIG. 3.

Figure 6A:
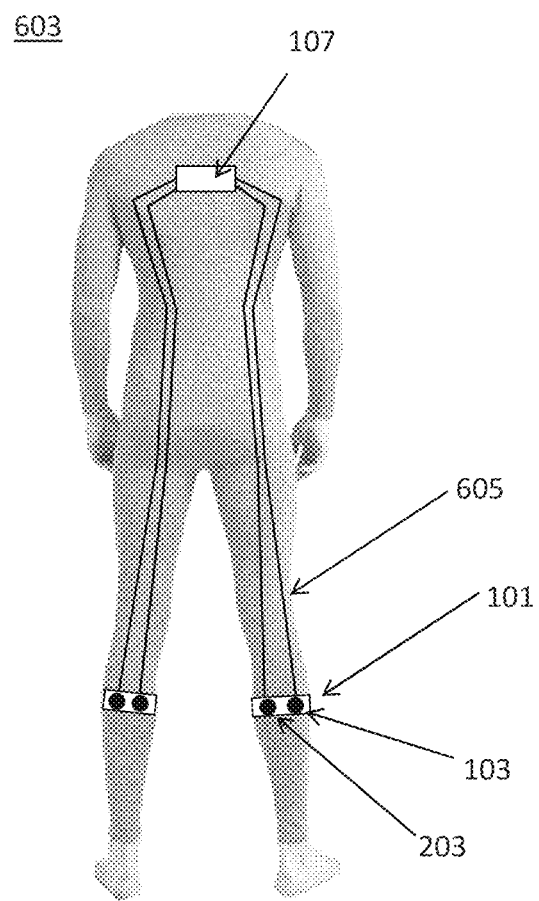
FIG. 6a shows a further variation to the embodiment of FIG. 3.

FIG. 6a shows a further variation of the embodiment of FIG. 3. The embodiment comprises a full body undergarment 603 having leggings 605. Along each legging 605 of the full body undergarment, about the position of the calf, is a resilient, stretchable, elastic band encircling the perimeter of the legging. Installed in the elastic band are a PPG sensor 203 as well as an electrode 103 of for obtaining an ECG.

Having an electrode 103 on both calves creates a closed circuit through the electrodes 103 across the body and heart of the person. The closed circuit is then useable for monitoring heart related electric signals. As in FIG. 3, a wire 105 is shown connecting the electrodes 103 to a flexible printed circuit board 107. The full body undergarment 603 has a wire extending from the printed circuit board 107 to the PPG in each legging, for controlling the PPG and collecting data from the PPG.

Accordingly, for each calf, an ECG can be obtained as well as a PPG. The ECG represents the time the heart beat producing the pulse takes place, and the PPG on each calf shows how long does it take for the pulse to travel from the heart to the calf, i.e. pulse-transit-time to the calf.

Any anomaly in the calf arteries may be monitored by the user wearing the full body undergarment, by observing differences in pulse-transit-time to each calf, the difference in amplitude between the pulses of the left leg and the right leg, the difference in spread between the pulses of the left leg and the right leg, and/or the difference in shape of the pulses of the left leg and the right leg, in the same manner as illustrated in FIG. 4, FIG. 5 and FIG. 5a for the upper limbs.

One useful application of this embodiment is in the quantification of 'pins-and-needles' or numbness suffered in the legs.

In another embodiment of the invention, a ballistocardiogram (BCG) sensor is placed on the clothing in place of the ECG. Alternatively the BCG sensor is placed in addition to the ECG. As the skilled man knows, a BCG sensor measures vibrational activity of the heart, i.e. ballistic forces. Generally, blood is ejected out from the heart into the ascending aorta and pulled into the heart from the inferior cava vein, in regular pumping motions. For both ejecting blood and pulling blood, according to Newton's 3rd Law, the force exerted on the blood by the heart is matched by an equal and opposite force on the body. These forces, or accelerations, can be detected by a sensitive accelerometer placed on the body, and the pumping of the blood can be deduced from the forces, to provide a chart which is the BCG.

Figure 7:
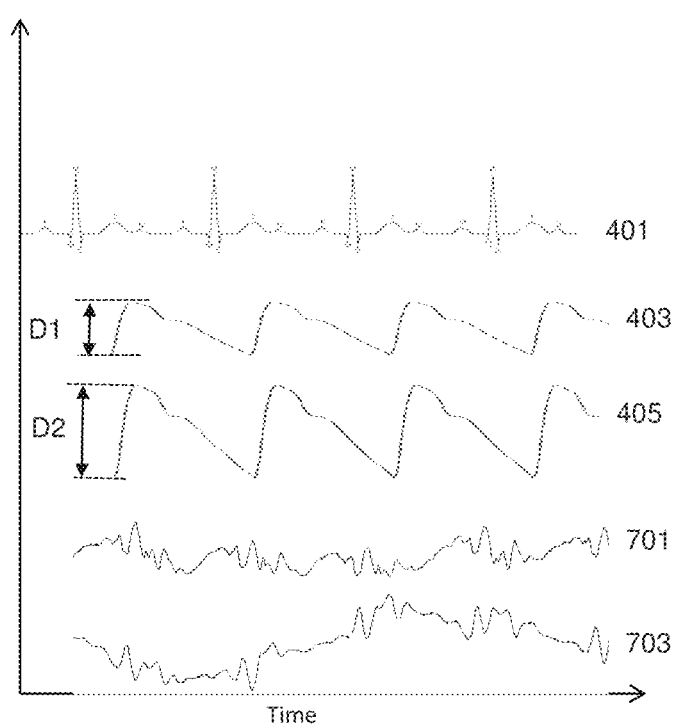
FIG. 7 shows a variation of the embodiment of FIG. 5.

FIG. 7 is a modification of FIG. 4, showing additionally two BCG signals. The BCG signals are modified from an actual chart in http://www.cs.tut.fi/sqn/SSSAG/BCG.htm, observed from a person seated in a chair that is slide-able with very low resistance. The top BCG 701 shows the acceleration of vibrations sensed by an accelerometer in in the back of a seat the person is seated on. The bottom BCG 701 shows the acceleration of vibrations sensed concurrently with the top BCG, but by an accelerometer located in the back of the same seat. The fluctuation of the baseline is caused by the person's normal breathing.

Figure 8:
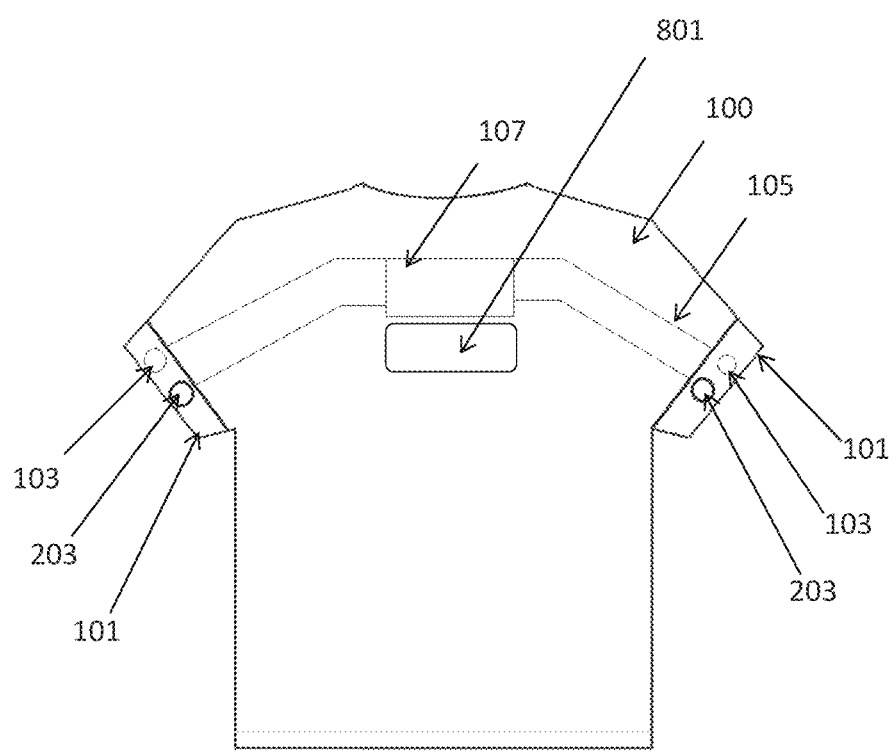
FIG. 8 shows a variation to the embodiment of FIG. 3.

FIG. 8 shows the embodiment of FIG. 3 modified to include a BCG sensor, which is typically an accelerometer 801. BCG sensor in this embodiment is placed at the back of the tee-shirt, where the upper back is. The BCG can then be used to compare with the PPG signals down one or both biceps of the person. The time lapse between the pulse observed in the BCG and the pulse observed by the PPGs of either bicep can be used to calculate pulse-transit-time, and deduce health, constriction and blockage in the arteries down the biceps.

Figure 9:
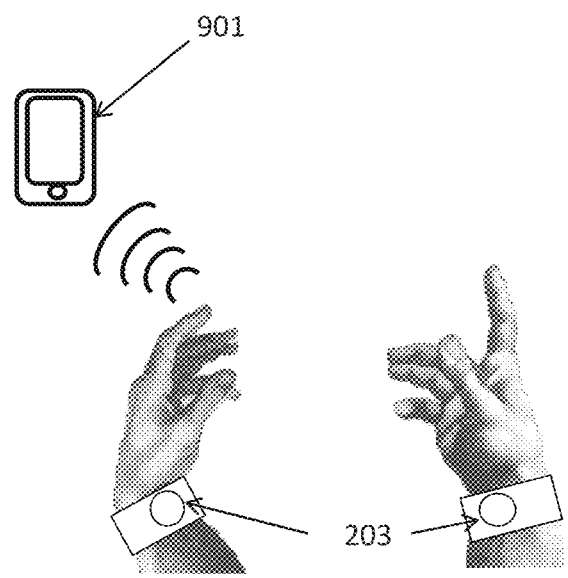
FIG. 9 shows an alternative embodiment to that of FIG. 3.
Figure 10:
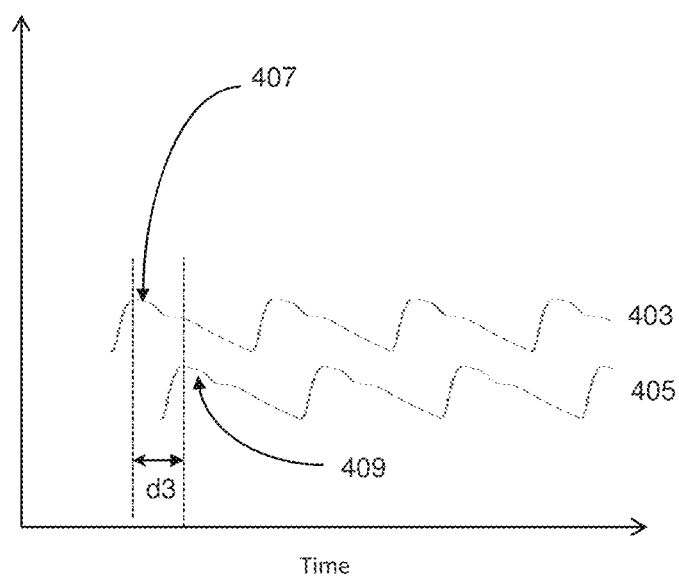
FIG. 10 shows data obtained by the embodiment of FIG. 9.

FIG. 9 shows one of the simplest embodiments of the invention, comprising only two wrist-worn PPG sensors 203. The PPG sensors 203 are in wireless communication with a mobile phone 901. The pulses read by each of the PPG sensors 203 are used to measure the time difference between them, as illustrated in FIG. 10, where d3 labels the time lag. In other words, the pulse-transit-time in each hand is not measured but the difference between the pulse-transit-times of both hands is measured directly. As the skilled man understands, the pulse in each hand must be created by the same heartbeat. Other comparisons of the PPPG pulse down each wrist may be made in the manner as described for FIG. 5 and FIG. 5a, for comparing the trough-to-peak amplitudes, and the spread of the pulses, as well as comparing the shapes of the pulses (not illustrated). In this embodiment, there is no ECG for a reference point by which to measure pulse-transit-time.

Embodiments have been described some of which comprises an apparatus for monitoring the pulse of a person, comprising a piece of clothing suitable for being worn on the body of the person; the clothing having two sleeves, each suitable for the person's respective limbs to be inserted through; along each of the sleeves is a stretchable neck 101 (the band in the sleeve 101 of FIG. 1, FIG. 2 or FIG. 3) for hugging the respective limb; one or more electrodes 103 in each neck 101; an electrical conductor 105 connecting the electrodes 103 of each neck 101; wherein the neck 101 urges the electrodes 103 of each of the sleeve into contact with the skin of the respective limb.

Furthermore, embodiments have been described some of which comprises an apparatus for monitoring the pulse of a person, comprising a piece of clothing suitable for being worn on the body of the person; the clothing having least one sleeve suitable for at least one of the person's limbs to be inserted through; the at least one sleeve having a resilient neck 101 for hugging the limb; one or more PPG sensors 203 in the neck 101; such that the neck 101 urges the one or more PPG sensors 203 into contact with the skin of the limb.

Also, embodiments have been described some of which comprises a method of monitoring heart pulses of a person, comprising the steps of: obtaining the left pulse of a heartbeat in the left limb; obtaining the right pulse of the same heartbeat in the right limb; observing a difference between the pulses in one or more of the following pulse characteristic: i. the pulse-transit-time of the pulse; ii. the spread of the pulse; iii. the trough to peak amplitude of the pulse; and/or iv. the shape of the pulse.

While there has been described in the foregoing description preferred embodiments of the present invention, it will be understood by those skilled in the technology concerned that many variations or modifications in details of design, construction or operation may be made without departing from the scope of the present invention as claimed.

For example, even though a tee-shirt has been described in most embodiments, any other kind of clothing such as jackets, formal shirts, overalls, pullovers and so on can be used as long as an elastic, resilient or stretchable part or parts are provided which strangle or hug the biceps, wrists, calves, ankles, fingers, toes, of the person in order to observe his pulses.

Although PPG has been described for measuring pulses in a person's limbs or extremities, other methods of observing the shape of a pulse is within the contemplation of the invention. For example, an atomic force microscope which uses a very sensitive cantilever for detecting the physical profile of a surface can be used to observe the shape of a pulse.

The invention claimed is:

1. An apparatus for monitoring the difference in pulses of a left side and a right side of a person, comprising:
   a piece of clothing suitable for being worn on a body of the person;
   the clothing having two sleeves, each suitable for the person's respective limbs to be inserted through;
   along each of the sleeves is a stretchable neck for hugging a respective limb;
   an electrocardiogram (ECG) device for detecting electrocardiogram (ECG) pulse, wherein:
      the piece of clothing further comprises one or more photoplethysmogram (PPG) sensors in the stretchable neck of each sleeve; such that the stretchable neck urges the one or more photoplethysmogram (PPG) sensors into contact with a skin of the respective limb, and
      a microcontroller configured to identify the electrocardiogram (ECG) pulse and the photoplethysmogram (PPG) pulse of each sleeves as being from the same heartbeat; wherein the microcontroller measures the pulse transit time between the ECG signal and the PPG signal.

2. The apparatus of claim 1, further comprising:
   a ballistocardiogram (BCG) sensor, wherein the microcontroller is configured to identify the electrocardiogram (ECG) pulse, a ballistocardiogram (BCG) pulse and the photoplethysmogram (PPG) pulses as being from the same heartbeat.

3. A method of monitoring the difference in pulses of a left and a right side of a person, comprising the steps of:
   obtaining an electrocardiogram (ECG) pulse of a heartbeat by the electrocardiogram (ECG);
   obtaining a left pulse of the same heartbeat in a left limb of an upper or a lower part of a body;
   obtaining a right pulse of the same heartbeat in a right limb in the same lower or the upper part of the body;
   observing a difference between the pulses in one or more of the following pulse characteristics:
      a pulse-transit-time of the pulse; wherein
      the left pulse of the heartbeat in the left limb is obtained by a photoplethysmogram (PPG), and the right pulse of the same heartbeat in the right limb is obtained by the photoplethysmogram (PPG); wherein the pulse-transit-time of the left pulse is referenced from the electrocardiogram (ECG) pulse;

the pulse-transit-time of the right pulse is referenced from the electrocardiogram (ECG) pulse; and comparing the pulses of the left limb and the right limb.

4. A method of claim 3, further comprising the step of:

obtaining a ballistocardiogram (BCG) pulse of the same heartbeat by the ballistocardiogram (BCG); wherein the pulse-transit-time of the left pulse is referenced from the ballistocardiogram (BCG) pulse; and the pulse-transit-time of the right pulse is referenced from the ballistocardiogram (BCG) pulse.

5. A method of claim 3, wherein the left limb is a left leg of the person; and the right limb is a right leg of the person.

6. A method of claim 5, wherein the left pulse of a heartbeat in the left limb is obtained from a left calf; and the right pulse of the same heartbeat in the right limb is obtained from a right calf.

* * * * *